(12) United States Patent
Koishi

(10) Patent No.: US 10,376,199 B2
(45) Date of Patent: Aug. 13, 2019

(54) IMAGING APPARATUS

(71) Applicant: KYOCERA Corporation, Kyoto-shi, Kyoto (JP)

(72) Inventor: Tomofumi Koishi, Tochigi (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/769,975

(22) PCT Filed: Oct. 26, 2016

(86) PCT No.: PCT/JP2016/004712
§ 371 (c)(1),
(2) Date: Apr. 20, 2018

(87) PCT Pub. No.: WO2017/073059
PCT Pub. Date: May 4, 2017

(65) Prior Publication Data
US 2018/0310868 A1 Nov. 1, 2018

(30) Foreign Application Priority Data
Oct. 26, 2015 (JP) .................. 2015-210095

(51) Int. Cl.
*H04N 7/18* (2006.01)
*A61B 5/18* (2006.01)
(Continued)

(52) U.S. Cl.
CPC ............. *A61B 5/18* (2013.01); *A61B 5/6893* (2013.01); *B60K 28/06* (2013.01); *G02B 1/115* (2013.01);
(Continued)

(58) Field of Classification Search
CPC ........ B60K 28/06; G02B 1/115; G03B 15/00; G08B 21/00; G06T 5/003; A61B 5/18;
(Continued)

(56) References Cited

U.S. PATENT DOCUMENTS

2012/0062787 A1 3/2012 Muijs et al.
2016/0037158 A1* 2/2016 Sugimoto ............ H04N 17/002
348/188
2016/0371821 A1* 12/2016 Hayashi ............... H04N 5/3572

FOREIGN PATENT DOCUMENTS

CN 203535250 A 4/2014
JP H8-290726 A 11/1996

OTHER PUBLICATIONS

Stechl, Data Sheet—Digital Photography Test & Practice, PC Magazin, Nov. 2011, www.pc-magazin.de/testbericht/nikon-1-v1-1209972-12846.html, 15 pages.

* cited by examiner

*Primary Examiner* — Robert Chevalier
(74) *Attorney, Agent, or Firm* — Procopio Cory Hargreaves and Savitch LLP

(57) ABSTRACT

An imaging apparatus with improved detection accuracy of the state of a subject is provided. An imaging apparatus comprises: an imaging optical system configured to form an optical image of a face of a subject in a vehicle; an image sensor configured to capture the formed optical image and generate a captured image; and an image processor configured to determine a state of the subject based on the captured image, wherein the imaging apparatus satisfies $F \geq 0.0003\ f^2/p$, where F is an F value of the imaging optical system, f is a focal length of the imaging optical system, and p is a pixel pitch of the image sensor.

5 Claims, 5 Drawing Sheets

(51) Int. Cl.
*B60K 28/06* (2006.01)
*G02B 1/115* (2015.01)
*G03B 15/00* (2006.01)
*G08B 21/00* (2006.01)
*H04N 5/232* (2006.01)
*A61B 5/00* (2006.01)
*G06K 9/00* (2006.01)
*G06T 5/00* (2006.01)
*H04N 9/47* (2006.01)

(52) U.S. Cl.
CPC ......... *G03B 15/00* (2013.01); *G06K 9/00496* (2013.01); *G06K 9/00845* (2013.01); *G06T 5/003* (2013.01); *G08B 21/00* (2013.01); *H04N 5/232* (2013.01); *G06T 2207/30196* (2013.01); *G06T 2207/30268* (2013.01)

(58) Field of Classification Search
CPC ............. A61B 5/6893; G06K 9/00496; G06K 9/00845; H04N 5/232; H04N 5/23212; H04N 5/23229; H04N 5/3572; H04N 5/3696; H04N 5/23238
USPC .......... 348/77, 61, 64, 78, 94; 386/210, 223, 386/224, 227
See application file for complete search history.

IMAGING APPARATUS

CROSS REFERENCE TO RELATED APPLICATION

This application claims priority to and the benefit of Japanese Patent Application No. 2015-210095 filed on Oct. 26, 2015, the entire disclosure of which is incorporated herein by reference.

TECHNICAL FIELD

An aspect of the present disclosure relates to an imaging apparatus for monitoring the state of a subject such as a driver of a vehicle.

BACKGROUND

Apparatuses for monitoring the state of a subject such as a driver of a vehicle are conventionally known.

SUMMARY

Solution to Problem

An imaging apparatus according to the present disclosure comprises: an imaging optical system configured to form an optical image of a face of a subject in a vehicle; an image sensor configured to capture the formed optical image and generate a captured image; and an image processor configured to determine a state of the subject based on the captured image, wherein the imaging apparatus satisfies F≥0.0003 f²/p, where F is an F value of the imaging optical system, f is a focal length of the imaging optical system, and p is a pixel pitch of the image sensor.

DETAILED DESCRIPTION

An embodiment of the present disclosure is described below, with reference to drawings.

A subject monitoring system 10 according to an embodiment of the present disclosure is described below, with reference to FIG. 1.

Figure 1:
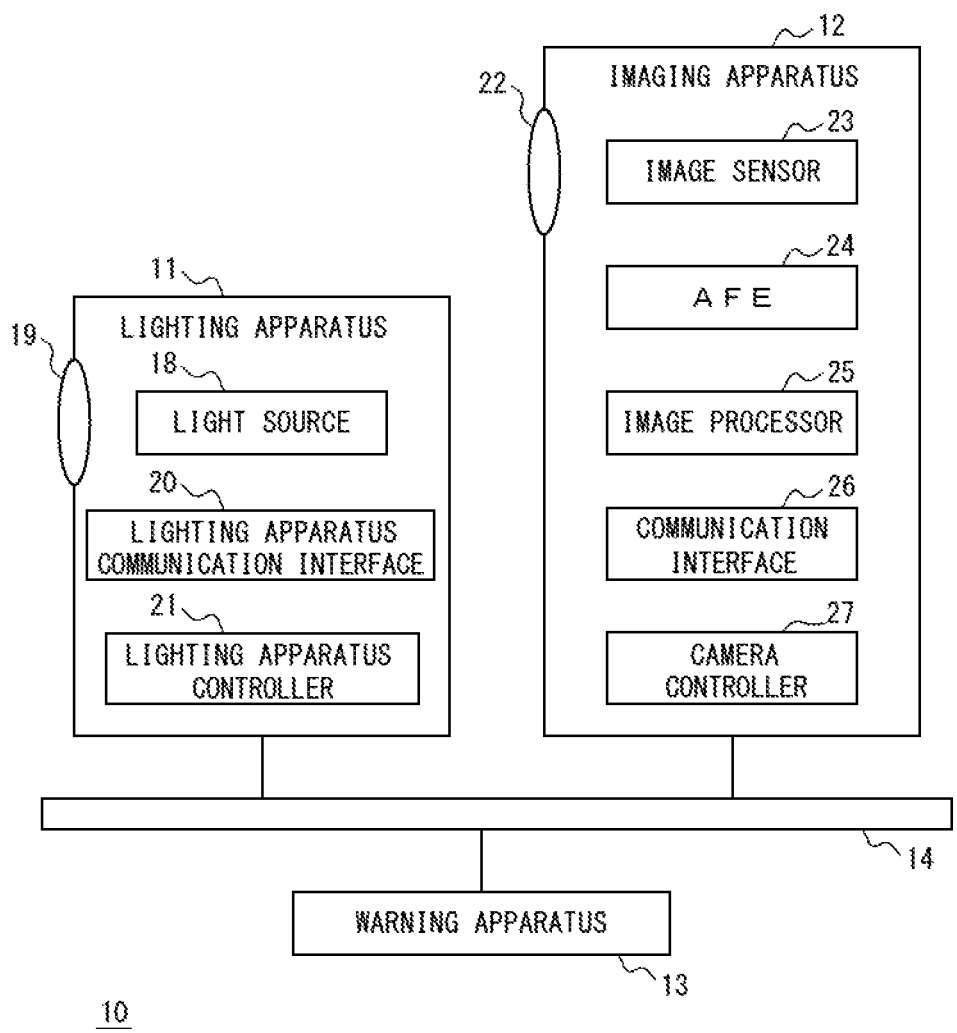
FIG. 1 is a block diagram illustrating the schematic structure of a subject monitoring system according to an embodiment.

As illustrated in FIG. 1, the subject monitoring system 10 includes a lighting apparatus 11, an imaging apparatus 12, and a warning apparatus 13. The components of the subject monitoring system 10 can transmit and receive information with each other via a network 14. The network 14 may include, for example, a wireless network, a wired network, or a Controller Area Network (CAN). In another embodiment, the components of the subject monitoring system 10 may be partly or wholly integrated as one apparatus.

Figure 2:
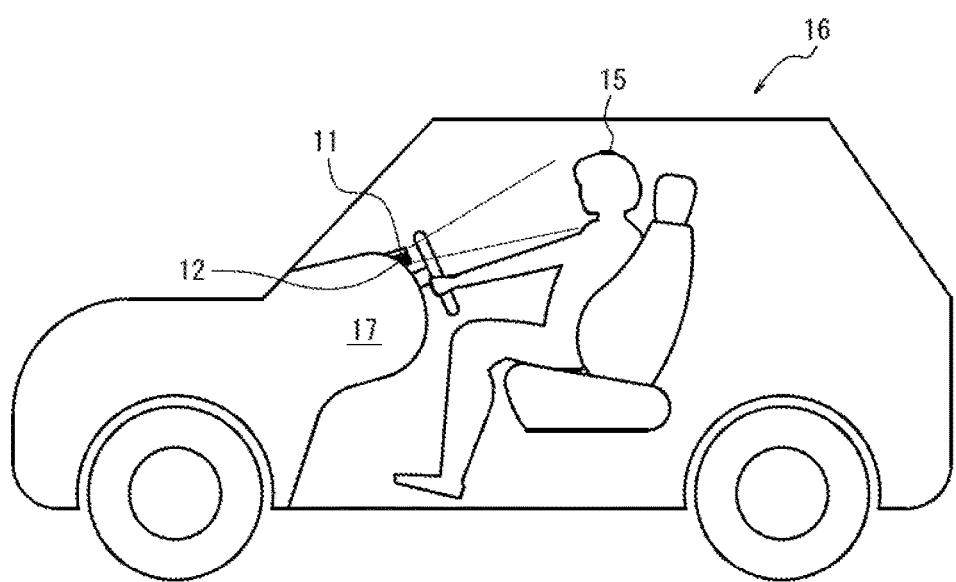
FIG. 2 is a left side view of a vehicle including the subject monitoring system in FIG. 1.

The lighting apparatus 11 is located at any position that enables the application of light to the face of a subject 15. The subject 15 may include, for example, a driver of a vehicle 16. For example, the lighting apparatus 11 may be installed on a dashboard 17 of the vehicle 16, as illustrated in FIG. 2. Light emitted from the lighting apparatus 11 is hereafter also referred to as illumination light.

The imaging apparatus 12 is located at any position that enables the capturing of the face of the subject 15. For example, the imaging apparatus 12 may be installed on the dashboard 17 of the vehicle 16. In an embodiment, the imaging apparatus 12 generates a captured image in which the pupils of the eyes of the subject 15 are bright. A captured image with bright pupils is hereafter also referred to as a bright pupil image. For example, the lighting apparatus 11 and the imaging apparatus 12 may be located close to each other, to enable the imaging apparatus 12 to generate a bright pupil image. In another embodiment, the imaging apparatus 12 generates a captured image in which the pupils of the eyes of the subject 15 are dark. A captured image with dark pupils is hereafter also referred to as a dark pupil image. For example, the lighting apparatus 11 and the imaging apparatus 12 may be located distant from each other, to enable the imaging apparatus 12 to generate a dark pupil image.

The warning apparatus 13 issues a warning to the subject 15. As an example, in the case of issuing a warning by sound, the warning apparatus 13 may be located at any position in the vehicle 16. As another example, in the case of issuing a warning by vibration, the warning apparatus 13 may be located at any position that enables the transmission of the vibration to the subject 15. For example, the warning apparatus 13 may be installed at a driver seat, a steering wheel, a shift knob, or a footrest in the vehicle 16.

Each component of the subject monitoring system 10 is described below.

The imaging apparatus 12 is described below. As illustrated in FIG. 1, the imaging apparatus 12 includes an imaging optical system 22, an image sensor 23, an analog front end (AFE) 24, an image processor 25, a communication interface 26, and a camera controller 27.

The imaging optical system 22 may include a diaphragm, at least one lens, and a lens barrel that holds these components. The imaging optical system 22 forms a subject image on the basis of light passing through the imaging optical system 22. The imaging optical system 22 allows at least light in a predetermined wavelength band to pass through. The predetermined wavelength band may include the wavelength of the illumination light emitted from the lighting apparatus 11, as described later. For example, in the case where the illumination light includes infrared light, the predetermined wavelength band may be a band encompassing wavelengths corresponding to the infrared light. In an embodiment, the imaging optical system 22 may further include a filter that allows light in the predetermined wavelength band to pass through. The imaging optical system 22 is located at any position that enables the reception of reflected light from the irradiation destination of the illumination light emitted from the lighting apparatus 11. In an embodiment, the imaging optical system 22 can form a subject image including the face of the subject 15 irradiated with the illumination light emitted from the lighting apparatus 11.

In the at least one lens included in the imaging optical system 22, an anti-reflective (AR) coating layer is formed on each of two or more lens surfaces. The AR coating layers may be formed by, for example, multi-coating. The AR coating layers enable the control of the transmittance of light in any band. For example, the transmittance of light in the visible band may be controlled. For example, the transmittance of light in any band may be controlled by forming AR coating layers with differing properties for each lens surface. In an embodiment, an AR coating layer is formed on each of two or more lens surfaces so that the transmittance of the illumination light emitted from the lighting apparatus 11 is higher than the transmittance of visible light. The transmittance of light by the AR coating layers will be described in detail later.

In an embodiment, the F value of the lens included in the imaging optical system 22 is determined depending on the pixel pitch of the image sensor 23. A method of determining the F value of the lens will be described in detail later.

The image sensor 23 may include, for example, a charge-coupled device (CCD) image sensor or a complementary metal oxide semiconductor (CMOS) image sensor. A plurality of pixels may be arranged at any pixel pitch on the light receiving surface of the image sensor 23. The image sensor 23 captures the subject image formed by the imaging optical system 22, to generate a captured image. In the case where the image sensor 23 includes a CMOS image sensor, the image sensor 23 may include the below-mentioned functions of the AFE 24.

The AFE 24 may include, for example, correlated double sampling (CDS), auto gain control (AGC), and an analog-to-digital converter (ADC). The AFE 24 performs predetermined upstream image processing on the analog captured image generated by the image sensor 23. The upstream image processing may include, for example, correlated double sampling, gain control, and A/D conversion.

The image processor 25 includes one or more processors. The processors may include a dedicated processor dedicated to a specific process, and a general-purpose processor that performs a specific function by reading a specific program. The dedicated processor may include a digital signal processor (DSP) and an application specific integrated circuit (ASIC). Each processor may include a programmable logic device (PLD). The PLD may include a field-programmable gate array (FPGA). The image processor 25 may be any of a system on a chip (SoC) or a system in a package (SiP) in which one or more processors cooperate with each other. The image processor 25 performs predetermined downstream image processing on the captured image on which the upstream image processing has been performed by the AFE 24.

The downstream image processing includes, for example, an exposure adjustment process. The downstream image processing may include a restoration process for reducing blurring in the captured image. The lens included in the imaging optical system 22 has an appropriate F value in order to obtain performance approximately equal to the diffraction limit in the whole region of the captured image, as mentioned below. In the diffraction limit, the response of the lens to a point light source is a rotationally symmetric sinc-function distribution. The response of the lens to a point light source may be expressed by, for example, the point spread function (PSF). In the case where the point spread function is an approximately uniform sinc-function distribution in the whole region of the captured image, blurring in the captured image can be reduced by using a single deconvolution filter corresponding to the point spread function. The deconvolution filter may include, for example, the Wiener filter. The image processor 25 performs the restoration process on the captured image, using a single deconvolution filter corresponding to the point spread function. The restoration process may include a deconvolution process.

The image processor 25 detects the eyes or pupils of the subject 15 in the captured image on which the downstream image processing has been performed. Any technique may be employed for the detection of the eyes or pupils. Examples of such techniques include methods that use pattern matching, and methods of extracting feature points (e.g. the feature points corresponding to the face contour, eyes, nose, and mouth) in the captured image. The feature points in the captured image may include, for example, the points corresponding to the face contour, eyes, pupils, nose, and mouth of the subject 15.

The image processor 25 determines the state of the subject 15 based on the detection result of the eyes or pupils of the subject 15 in the captured image. For example, if the subject 15 is driving inattentively or drowsily, the image processor 25 may be unable to detect the eyes or pupils of the subject 15 in the captured image for a plurality of consecutive frames. The state in which the subject 15 is driving inattentively or drowsily is hereafter also referred to as an inappropriate driving state. The image processor 25 may determine that the subject 15 is in an inappropriate driving state in the case where the eyes or pupils of the subject 15 in the captured image have not been detected for a predetermined number of consecutive frames.

The image processor 25 may generate a control signal for causing the warning apparatus 13 to issue a warning, depending on the determination result of the state of the subject 15. The image processor 25 may output the control signal to the warning apparatus 13 via the communication interface 26. In an embodiment, the image processor 25 generates and outputs the control signal in the case where the subject 15 is determined to be in an inappropriate driving state.

The communication interface 26 may include an interface that performs information input and output via the network 14. Information input is hereafter also referred to as information acquisition or reception. Information output is hereafter also referred to as information transmission.

The camera controller 27 includes one or more processors. The processors may include a dedicated processor dedicated to a specific process, and a general-purpose processor that performs a specific function by reading a specific program. The dedicated processor may include an ASIC. Each processor may include a PLD. The PLD may include an FPGA. The camera controller 27 may be any of a SoC or a SiP in which one or more processors cooperate with each other. The camera controller 27 controls the operation of the whole imaging apparatus 12. For example, the camera controller 27 generates a synchronization signal indicating imaging timing, and controls the operation of the communication interface 26 to output the synchronization signal to the lighting apparatus 11. Upon outputting the synchronization signal, the camera controller 27 controls the operation of the image sensor 23 to capture the subject image. In another embodiment, the synchronization signal may be generated by an apparatus included in the vehicle 16 other than the imaging apparatus 12. For example, the synchronization signal may be generated by the lighting apparatus 11, the warning apparatus 13, or an electronic control unit (ECU) mounted in the vehicle 16. The generated synchronization signal may be output to each of the imaging apparatus 12 and the lighting apparatus 11.

The lighting apparatus 11 is described below. The lighting apparatus 11 includes at least one light source 18, a lighting optical system 19, a lighting apparatus communication interface 20, and the lighting apparatus controller 21.

The light source 18 includes, for example, an LED. The light source 18 emits at least light in the predetermined wavelength band. Light emission by the light source 18 may be continuous light emission or pulse light emission. Light in the predetermined wavelength band is light that can be photoelectrically converted by the image sensor 23 in the imaging apparatus 12. In an embodiment, the light source 18 may be an infrared LED that emits diffused light in the infrared band.

The lighting optical system 19 includes, for example, a lens whose angle of view has been adjusted. The lighting optical system 19 applies light passing through the lighting optical system 19. In an embodiment, illumination light emitted from the light source 18 and passed through the lighting optical system 19 is applied to the entire face of the subject 15.

The lighting apparatus communication interface 20 includes an interface that performs information input and output via the network 14.

The lighting apparatus controller 21 includes one or more processors. The processors may include a dedicated processor dedicated to a specific process, and a general-purpose processor that performs a specific function by reading a specific program. The dedicated processor may include an ASIC. Each processor may include a PLD. The PLD may include an FPGA. The lighting apparatus controller 21 may be any of a SoC or a SiP in which one or more processors cooperate with each other. The lighting apparatus controller 21 controls the operation of each part of the lighting apparatus 11. For example, the lighting apparatus controller 21 causes the light source 18 to emit light, synchronously with the imaging timing of the imaging apparatus 12. In an embodiment, the lighting apparatus controller 21 periodically causes the light source 18 to emit light in the infrared band for a predetermined time, according to the synchronization signal acquired via the lighting apparatus communication interface 20. The imaging apparatus 12 performs imaging according to the synchronization signal, as mentioned earlier. Thus, the light emission timing of the lighting apparatus 11 and the imaging timing of the imaging apparatus 12 coincide with each other.

The warning apparatus 13 is described below. The warning apparatus 13 may include, for example, a speaker and a vibrator. The warning apparatus 13, upon receiving the above-mentioned control signal from the imaging apparatus 12, issues a warning to the subject 15. The warning may be issued as, for example, at least one of sound and vibration. Based on the warning, it is possible to remind the subject 15 who is, for example, driving inattentively or drowsily, to pay more attention to driving.

Figure 3:
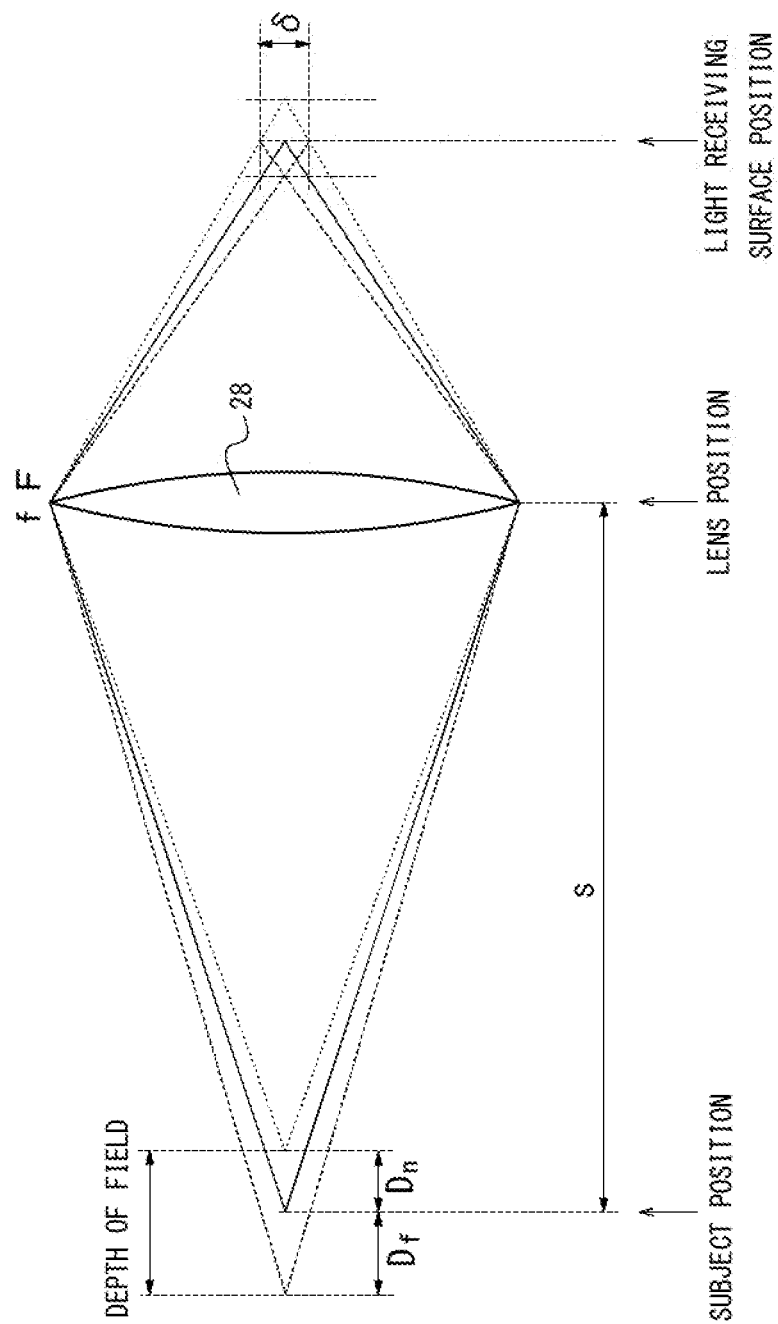
FIG. 3 is a sectional diagram along an optical axis illustrating the schematic structure of a lens included in an imaging optical system.

The lens 28 included in the imaging optical system 22 in the imaging apparatus 12 and a method of determining the F value of the lens 28 are described in detail below, with reference to FIG. 3. The lens 28 focuses light incident from the object side, to form an image at the light receiving surface position of the image sensor 23. Hereafter, the focal length of the lens 28 is denoted by f [mm], the F value is denoted by F, the back depth of field is denoted by $D_n$ [mm], the front depth of field is denoted by $D_f$ [mm], the imaging distance is denoted by S [mm], the permissible confusion circle diameter is denoted by δ [mm], and the pixel pitch of the image sensor 23 is denoted by p [mm].

The depth of field (back depth of field $D_n$+front depth of field $D_f$) is defined by the following Expression (1):

$$D_n + D_f = \frac{\delta F(s-f)^2}{f^2 + \delta F(s-f)} + \frac{\delta F(s-f)^2}{f^2 - \delta F(s-f)} \tag{1}$$

The imaging distance between the imaging apparatus 12 and the subject 15 can vary depending on the individual difference or position of the subject 15. In the subject monitoring system 10, predetermined system requirements may be imposed on the imaging apparatus 12 so that an expected imaging range of the imaging distance is within the depth of field. For example, the system requirements may be set according to the vehicle constants of the vehicle 16 and the location of the imaging apparatus 12 in the vehicle 16. In an embodiment, for example, four system requirements: the imaging range, the horizontal angle of view θ, the pixel pitch p, and the permissible confusion circle diameter δ, are taken into consideration. Examples of the values of the respective system requirements are given below:

imaging range: 400 mm to 1000 mm horizontal angle of view θ: 30° to 60° pixel pitch p: 0.003 mm to 0.006 mm permissible confusion circle diameter δ: δ=2p.

The focal length f satisfying the above-mentioned system requirements is described below. The focal length f is calculated for various combinations of different values of the system requirements. Each focal length f is calculated using the following Expression (2):

$$h = f \times \tan(\theta/2) \tag{2}$$

where h [mm] is the image height.

Each of the pixel pitch p, the number of horizontal pixels of the image sensor 23, and the horizontal angle of view θ is varied to calculate a plurality of focal lengths f. The pixel pitch p may be varied, for example, in a range of 0.003 mm to 0.006 mm. The number of horizontal pixels may be varied, for example, in a range of 640 pixels to 1920 pixels. The horizontal angle of view θ may be varied, for example, in a range of 30° to 60°. Some calculated focal lengths f are listed in the following Table 1. Table 1 lists the focal lengths f calculated to satisfy the above-mentioned system requirements, for ten combinations in the case where the pixel pitch p is 0.006 mm or 0.003 mm, the number of horizontal pixels of the image sensor 23 is 640 pixels, 1280 pixels, or 1920 pixels, and the horizontal angle of view θ is 30°, 50°, or 60°.

TABLE 1

| | Pixel pitch p [mm] | | | | | | | | | | | |
|---|---|---|---|---|---|---|---|---|---|---|---|---|
| | 0.006 | | | | | | 0.003 | | | | | |
| | Number of horizontal pixels | | | | | | | | | | | |
| | 640 | | | 1280 | | | 1280 | | | 1920 | | |
| | Horizontal angle of view [°] | | | | | | | | | | | |
| | 30 | 50 | 60 | 30 | 50 | 60 | 30 | 50 | 60 | 30 | 50 | 60 |
| Focal length f [mm] | 7.17 | 4.12 | 3.33 | — | 8.23 | 6.65 | 7.17 | 4.12 | — | 10.75 | 6.18 | 4.99 |

The lower limit value of the F value satisfying the above-mentioned system requirements is calculated using each calculated focal length f. The lower limit value of the F value is calculated using the foregoing Expression (1). For example, the lower limit value of the F value is calculated for each focal length f in the case where the pixel pitch p is 0.006 mm or 0.003 mm, the number of horizontal pixels is 640 pixels, 1280 pixels, or 1920 pixels, and the horizontal angle of view θ is changed from 30° to 60°.

Figure 4:
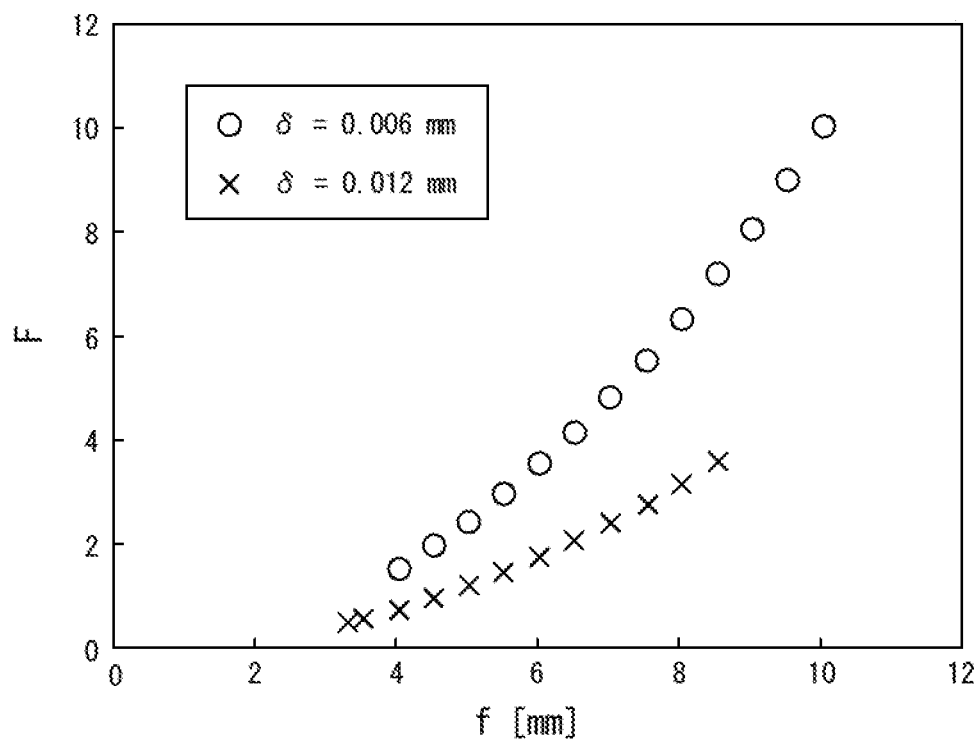
FIG. 4 is a diagram illustrating the relationship between the focal length and the F value.

FIG. 4 is a graph obtained by plotting each calculated F value, with the horizontal axis representing the focal length f and the vertical axis representing the F value. FIG. 4 illustrates the lower limit value of the F value in the case where the pixel pitch p=0.003 mm, and the lower limit value of the F value in the case where the pixel pitch p=0.006 mm. In the case where the pixel pitch p=0.003 mm, the permissible confusion circle diameter δ=2p=0.006 mm. In the case where the pixel pitch p=0.006 mm, the permissible confusion circle diameter δ=2p=0.012 mm.

Figure 5:
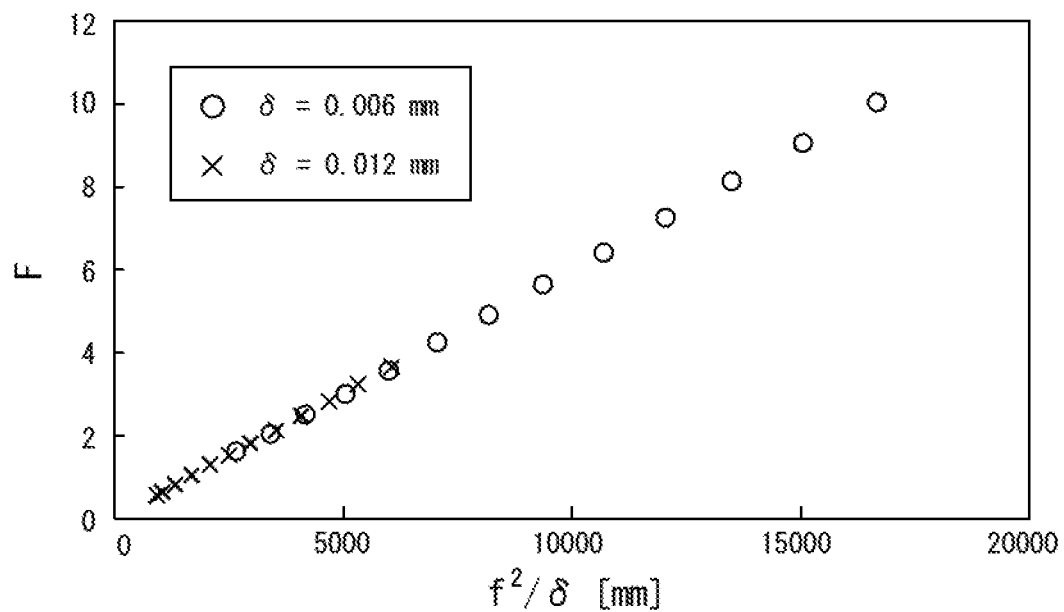
FIG. 5 is a diagram illustrating the relationship between (the square of the focal length)/(the permissible confusion circle diameter) and the F value.

FIG. 5 is a graph obtained by re-plotting each lower limit value of the F value illustrated in FIG. 4, with the horizontal axis representing $f^2/\delta$. In FIG. 5, the slope of a straight line passing through each plotted point is 0.0006, and its intercept is 0. Hence, the range of the F value satisfying the above-mentioned system requirements is represented by the following Expression (3):

$$F \geq 0.0003 \, f^2/p \quad (3).$$

By determining the F value of the lens 28 so as to satisfy the foregoing Expression (3), the imaging apparatus 12 can satisfy the above-mentioned system requirements.

However, simply increasing the F value can cause the captured image to become darker, unless, for example, the output of the illumination light by the lighting apparatus 11 is increased. This is likely to cause a decrease in detection accuracy of the state of the subject 15 or render the detection impossible. Meanwhile, for example in terms of heat generation or power consumption, it may be impossible to increase the output of the illumination light by the lighting apparatus 11. In view of this, an appropriate upper limit value of the F value may be determined.

The lens 28 with a high F value eases design aberration correction, and has low tolerance sensitivity. Accordingly, with the imaging optical system 22 including the lens 28 with a high F value, performance approximately equal to the diffraction limit can be achieved in the whole region of the captured image. The whole region of the captured image may correspond to the whole light receiving surface of the image sensor 23. Meanwhile, in the case where the F value is higher than necessary, resolution performance is limited by the diffraction limit. The resolution performance may be resolving power. Therefore, a minimum F value with which performance approximately equal to the diffraction limit can be achieved may be determined, and set as the upper limit value of the F value. A method of determining the upper limit value of the F value is described in detail below.

The diameter φ of the Airy disk in the diffraction limit is given by the following Expression (4):

$$\varphi = 2.44 \lambda F \quad (4)$$

where λ is the wavelength of the light. In an embodiment, λ is the center wavelength of the illumination light in the infrared band from the lighting apparatus 11.

In relation to this embodiment, it has been experimentally revealed that performance approximately equal to the diffraction limit can be achieved practically in the case where the relationship between the diameter φ of the Airy disk and the pixel pitch p satisfies the following Expression (5):

$$\varphi \leq 4p \quad (5).$$

From the foregoing Expressions (4) and (5), the range of the F value is represented by the following Expression (6):

$$F \leq 1.64 \, p/\lambda \quad (6).$$

By determining the F value of the lens 28 so as to satisfy the foregoing Expression (6), the imaging apparatus 12 can achieve performance approximately equal to the diffraction limit in the whole region of the captured image.

The transmittance of light by the AR coating layers formed on at least one optical member included in the imaging optical system 22 is described in detail below, with reference to FIG. 6. In an embodiment, the optical member includes the lens 28. Four types of structure in the case where the number of AR coating layers formed on one lens surface is 1 layer or 2 layers and the number of lens surfaces each subjected to AR coating layer formation is 4 surfaces or 6 surfaces are described below.

Figure 6:
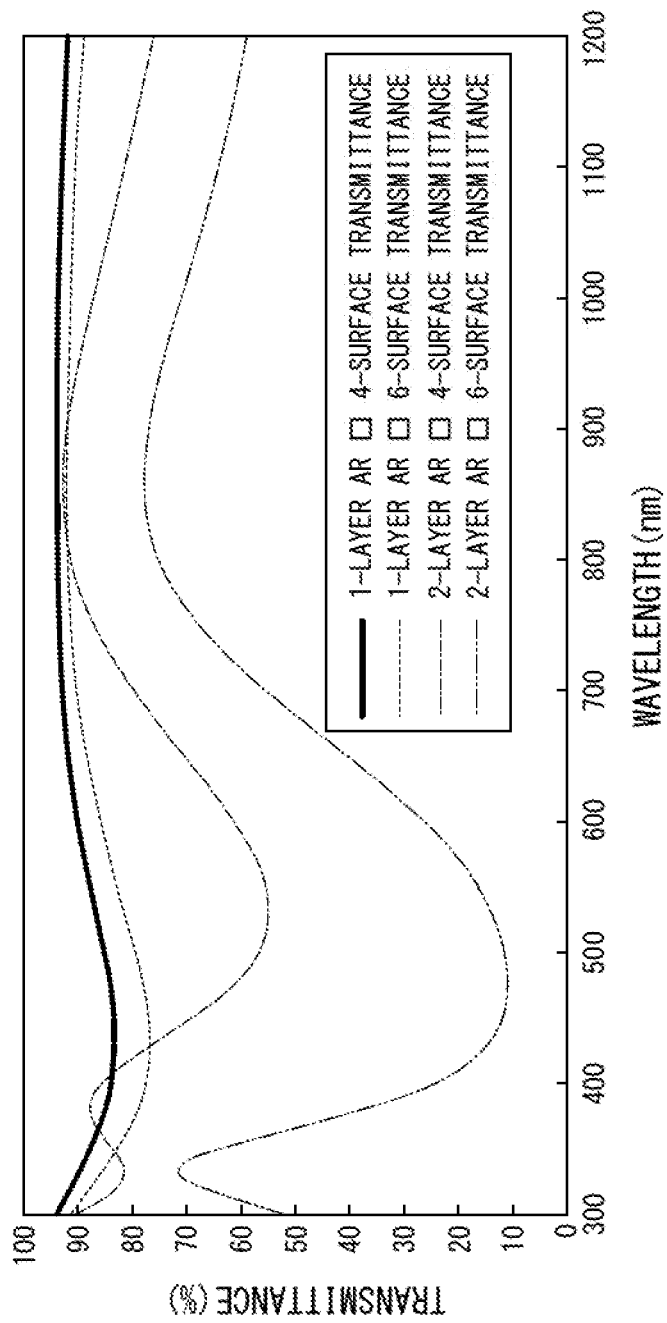
FIG. 6 is a diagram illustrating the transmittance of light of the imaging optical system for each wavelength, according to the number of coated surfaces and the number of AR coating layers of the lens included in the imaging optical system.

FIG. 6 is a graph in which the horizontal axis represents the light wavelength λ [nm] and the vertical axis represents the light transmittance [%]. FIG. 6 illustrates the relationship between the wavelength and the transmittance, for each of: a structure A in which the number of AR coating layers is 1 layer and the number of lens surfaces is 4 surfaces; a structure B in which the number of AR coating layers is 1 layer and the number of lens surfaces is 6 surfaces; a structure C in which the number of AR coating layers is 2 layers and the number of lens surfaces is 4 surfaces; and a structure D in which the number of AR coating layers is 2 layers and the number of lens surfaces is 6 surfaces. In the drawing, the solid line corresponds to the structure A, the dash line corresponds to the structure B, the dash dot line corresponds to the structure C, and the dash double dot line corresponds to the structure D.

In an embodiment, the transmittance of light in the visible band is reduced by the AR coating layers, while the transmittance of light in the infrared band from the lighting apparatus 11 is maintained at a comparatively high value. The visible band may include, for example, a wavelength band of 360 nm to 760 nm. The infrared band may include, for example, a wavelength band of 850 nm to 940 nm. In the structure A and the structure B in which the number of AR coating layers is 1 layer, magnesium fluoride ($MgF_2$) is used for the AR coating layer. $MgF_2$ is a low refractive index material that transmits light ranging from deep ultraviolet to near infrared. In the structure C in which the number of AR coating layers is 2 layers, $MgF_2$ is used for a first layer, and zirconium dioxide ($ZrO_2$) is used for a second layer. $ZrO_2$ is a high refractive index material that transmits light ranging from 340 nm to 8 μm. In the structure D in which the number of AR coating layers is 2 layers, $MgF_2$ is used for a first layer, and titanium oxide ($TiO_2$) is used for a second layer. $TiO_2$ is a high refractive index material that absorbs light in the ultraviolet band.

As illustrated in FIG. 6, in the structure A and the structure B in which the number of AR coating layers is 1 layer, for example, the transmittance near 420 nm is about 80%, and so the transmittance in the visible band is comparatively high. In the structure C in which the number of AR coating layers is 2 layers and the number of lens surfaces is 4 surfaces, for example, the transmittance near 530 nm is about 55%, and so the transmittance in the visible band is lower than those of the structure A and the structure B.

In the structure D in which the number of AR coating layers is 2 layers and the number of lens surfaces is 6 surfaces, for example, the transmittance near 480 nm is about 10%, and so the transmittance in the visible band is lower than that of the structure C. Moreover, for example, while the transmittance near 400 nm is about 85% in the structure C, the transmittance near 400 nm is about 25% in the structure D. Likewise, for example, while the transmittance near 700 nm is about 80% in the structure C, the transmittance near 700 nm is about 55% in the structure D. Thus, the structure D has reduced transmittance throughout the visible band, as compared with the structure C. The structure of the imaging optical system 22 according to this embodiment is not limited to the structure C and the structure D. Different types of AR coating layers may be formed on two or more lens surfaces. For example, the types of AR coating layers may differ by the material(s) contained in the AR coating layer and/or the number of layers formed. As an example, an AR coating layer formed on a given lens surface may comprise a first layer containing $MgF_2$ and a second layer containing $ZrO_2$, and an AR coating layer formed on another lens surface may comprise a first layer containing $MgF_2$ and a second layer containing $TiO_2$. Desired wavelength property can be achieved by adjusting the type of AR coating layer formed on each of two or more lens surfaces.

In an embodiment, the F value of the lens 28 is comparatively high, as mentioned earlier. Accordingly, light in the visible band from among outside light comparatively decreases in intensity as a result of passing through the lens 28. For example, in the case where the intensity of illumination light by the lighting apparatus 11 is sufficiently high as compared with the intensity of outside light, a captured image suitable for practical use can be obtained by reducing outside light by a prescribed amount by a plurality of AR coating layers as described above. Unlike a structure in which the imaging optical system includes a visible light cutoff filter, no visible light cutoff filter is needed, and thus the imaging optical system 22 can be simplified in structure and reduced in size.

As described above, the lens 28 in the imaging apparatus 12 according to an embodiment may be determined so as to satisfy the foregoing Expression (1): $F \geq 0.0003\ f^2/p$, using the F value, the focal length f, and the pixel pitch p of the image sensor 23. With such a structure, the imaging apparatus 12 can be used even in a special use environment such as being installed in the vehicle 16 to capture an image of the subject 15.

An example where an imaging apparatus other than the imaging apparatus 12 according to an embodiment is used is described below. Since the space inside the vehicle is limited and the imaging distance from the imaging apparatus to the subject is short, the depth of field of the imaging apparatus is shallow. The imaging distance can vary depending on, for example, the individual difference or position of the subject. Accordingly, if the depth of field is shallow, there is a possibility that the subject is out of focus and the captured image is blurred. Blurring in the captured image is likely to cause a decrease in detection accuracy of the state of the subject.

The imaging apparatus 12 according to an embodiment, on the other hand, can ensure a sufficient depth of field for capturing, for example, an image of the subject 15 whose position can vary in the vehicle 16. This prevents blurring in the captured image, and improves the detection accuracy of the state of the subject 15.

In the case where $F=0.0003\ f^2/p$, a comparatively bright captured image is generated while ensuring the depth of field. The detection accuracy of the state of the subject 15 can thus be further improved in terms of the brightness of the captured image.

A high F value can be set according to the foregoing Expression (1). A high F value enables a small aperture of the lens 28. This makes it possible to reduce the size of the lens barrel of the imaging optical system 22, and so reduce the size of the imaging apparatus 12 as a whole. A high F value eases aberration correction. Hence, the number of lenses in the imaging optical system 22 can be reduced and the size of the imaging apparatus 12 as a whole can be reduced as compared with, for example, a structure using a lens with $F<0.0003\ f^2/p$, i.e. not satisfying the foregoing Expression (1). A high F value increases the focal depth. Hence, a margin for the defocus characteristic is obtained as compared with, for example, a structure using a lens with $F<0.0003\ f^2/p$, i.e. not satisfying the foregoing Expression (1). This facilitates the use of, for example, a resin lens having a higher linear expansion coefficient than a glass lens. Choices of usable lenses thus diversify. Resin lenses having various properties are usable, with it being possible to further reduce the size of the imaging apparatus 12 as a whole.

The F value of the lens 28 may be determined so as to satisfy the foregoing Expression (6): $F \leq 1.64\ p/\lambda$, using the center wavelength λ of the illumination light that illuminates the subject 15. With such a structure, the imaging apparatus 12 achieves a favorable balance between the resolution performance by the diffraction limit and the brightness of the captured image.

An example where an imaging apparatus other than the imaging apparatus 12 according to an embodiment is used is described below. One way of increasing the depth of field might be to increase the F value of the imaging apparatus. If the F value is increased, however, the captured image becomes darker. This is likely to cause a decrease in detection accuracy of the state of the subject or render the detection impossible.

In the imaging apparatus 12 according to an embodiment, on the other hand, with the imaging optical system 22 including the lens 28 with $F=1.64\ p/\lambda$, performance approximately equal to the diffraction limit can be achieved in the whole region of the captured image, so that resolution performance can be improved. With the imaging optical system 22 including the lens 28 with F<1.64 p/λ, resolution performance can decrease but a bright captured image can be obtained, as compared with the case where the F value of the lens 28 is F=1.64 p/λ. Such an imaging apparatus 12 can be used even in the case where the output of the lighting apparatus 11 is unable to be increased in terms of heat generation, power consumption, or the like. In a structure that uses a lens with F>1.64 p/λ, i.e. not satisfying Expression (6), resolution performance does not change due to the diffraction limit, but the captured image may become darker. This is likely to cause a decrease in detection accuracy of the state of the subject 15, as compared with the case where Expression (6) is satisfied.

The imaging apparatus 12 may perform a restoration process on the captured image, using a single deconvolution filter. By determining the F value of the lens 28 so as to satisfy Expression (3) and make the depth of field sufficiently deep, the point spread function becomes an approximately uniform sinc-function distribution in the whole region of the captured image, as mentioned earlier. In other words, by using the lens 28 whose depth of field is deep, the imaging apparatus 12 can be designed so that the spread of the point image throughout the imaging distance has a prescribed distribution. In detail, the illumination light by the lighting apparatus 11 is light in the infrared band having a predetermined center wavelength, and chromatic aberration is practically negligible. Therefore, when the aperture of the lens 28 is decreased, the spread of the point image has an approximately uniform distribution in the whole region of the captured image. Moreover, the lens 28 with a high F value has low tolerance sensitivity, as mentioned earlier. Performance close to a design value can thus be achieved. Hence, blurring in the captured image can be reduced by using a single deconvolution filter corresponding to the point spread function. This lightens the processing load as compared with, for example, a structure in which the point spread function is not uniform in the whole region of the captured image and a restoration process is performed using a plurality of filters. In the case where performance is close to the diffraction limit, the filter size can be reduced.

Different types of coating layers may be formed on two or more lens surfaces of at least one lens included in the imaging optical system 22. With such a structure, desired wavelength property can be obtained. For example, the transmittance in the infrared band can be increased while decreasing the transmittance in the visible band and the ultraviolet band. Unlike a structure in which the imaging optical system includes a visible light cutoff filter, no visible light cutoff filter is needed, and thus the imaging optical system 22 can be simplified in structure and reduced in size.

While the disclosed apparatus has been described by way of the drawings and embodiments, various changes or modifications may be easily made by those of ordinary skill in the art based on the present disclosure. Such various changes or modifications are therefore included in the scope of the present disclosure. For example, the functions included in the means, steps, etc. may be rearranged without logical inconsistency, and a plurality of means, steps, etc. may be combined into one means, step, etc. and a means, step, etc. may be divided into a plurality of means, steps, etc.

Part of the components of the subject monitoring system 10 according to the embodiment described above may be provided outside the vehicle 16. For example, the imaging apparatus 12 may be implemented as communication equipment such as a mobile phone, and connected to the other components of the subject monitoring system 10 by wired or wireless means.

The invention claimed is:

1. An imaging apparatus comprising:
an imaging optical system configured to form an optical image of a face of a subject in a vehicle;
an image sensor configured to capture the formed optical image and generate a captured image; and
an image processor configured to determine a state of the subject based on the captured image,
wherein the imaging apparatus satisfies the expression $F \geq 0.0003\ f^2/p,$ where F is an F value of the imaging optical system, f is a focal length of the imaging optical system, and p is a pixel pitch of the image sensor.

2. The imaging apparatus according to claim 1, wherein the imaging apparatus satisfies the expression:

$F \leq 1.64\ p/\lambda,$ where λ is a wavelength of illumination light that illuminates the subject.

3. The imaging apparatus according to claim 1, wherein the image processor is configured to perform a restoration process on the captured image, using a single deconvolution filter.

4. The imaging apparatus according to claim 3, wherein the deconvolution filter is a filter corresponding to a point spread function indicating a rotationally symmetric sinc-function distribution.

5. The imaging apparatus according to claim 1, wherein the imaging optical system includes at least one lens, with different types of coating layers being formed on two or more lens surfaces thereof, and transmittance of illumination light that illuminates the subject is higher than transmittance of visible light.

* * * * *